United States Patent [19]

Haskell et al.

[11] 4,404,201

[45] Sep. 13, 1983

[54] CEPHALOSPORINS

[75] Inventors: Theodore H. Haskell, Ann Arbor; Marland P. Hutt, Saline, both of Mich.

[73] Assignee: Warner-Lambert Company, Morris Plains, N.J.

[21] Appl. No.: 321,021

[22] Filed: Nov. 13, 1981

[51] Int. Cl.$^3$ .................. A61K 31/545; C07D 501/34
[52] U.S. Cl. ..................... 424/246; 544/22; 544/27; 544/28
[58] Field of Search ................. 424/246; 544/22, 27, 544/28

[56] References Cited

U.S. PATENT DOCUMENTS 4,156,724  5/1979  Yamada et al. ................. 544/27
4,311,698  1/1982  Haskell et al. ................. 544/27

Primary Examiner—Paul M. Coughlan, Jr.
Attorney, Agent, or Firm—Jerry F. Janssen

[57] ABSTRACT

Novel organic amide compounds which are N-[[(acylaminoacylamino or aminoacylamino)]-dihydro-oxo-3-quinolinylcarbonyl]cephalosporin compounds having broad spectrum antibacterial utility are provided by (a) reacting the free amino acid of the appropriate cephalosporin or the acid addition salt or silylated derivative or complex thereof with a reactive derivative of the corresponding (acylaminoacylamino or aminoacylamino)dihydro-oxo-3-quinolinecarboxylic acid or (b) reacting the free amino acid 7-aminocephalosporanic acid or a related compound or the acid salt or silylated derivative thereof with a reactive derivative of the corresponding D-N-[(acylaminoacylamino or aminoacylamino)dihydro-oxo-3-quinolinylcarbonyl]-2-substituted glycine. Pharmaceutical compositions containing said compounds and methods for treating infections using said compositions are also disclosed.

15 Claims, No Drawings

CEPHALOSPORINS

SUMMARY AND DETAILED DESCRIPTION

The present invention relates to novel chemical compounds that are useful as pharmacological agents and to methods for their production. More particularly, the invention relates to novel organic amide compounds having the formula

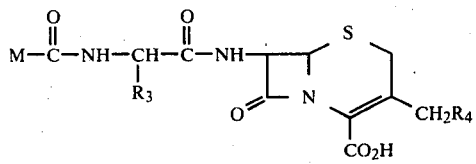

and pharmaceutically acceptable salts thereof; wherein M is

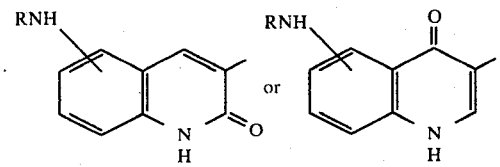

R is

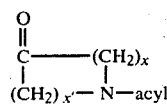

or $R_1$-[$R_5$N-acyl]$_n$; x is an integer from one to five, x' is zero, one or two; $R_1$ is hydrogen, lower alkyl, benzyl, or $$R_2\overset{O}{\underset{\|}{C}}-$$

wherein $R_2$ is hydrogen, amino or a lower alkyl group of from one to four carbon atoms, optionally substituted by from one to three chlorine or fluorine atoms; $R_5$ is hydrogen or lower alkyl and N-acyl is an aminoacyl moiety derived from a carboxylic acid of from two to ten carbon atoms optionally substituted by from one to three of the following groups, hydroxyl, carboxy, $$H_2N-\overset{O}{\underset{\|}{C}}, \text{(lower alkyl) } NH-\overset{O}{\underset{\|}{C}}, \text{(lower alkyl)}_2N-\overset{O}{\underset{\|}{C}},$$

formamido, lower alkyl-$\overset{O}{\underset{\|}{C}}$—O, H—$\overset{O}{\underset{\|}{C}}$—O, amino, alkylamido, carbamido, carbonyl oxygen, lower alkoxy, lower alkylthio or sulfonic acid, n is an integer of from one to four; $R_3$ is phenyl, 4-hydroxyphenyl, 2-thienyl or cyclohexa-1,4-dien-1-yl and $R_4$ is acetoxy, carbamoyloxy, or a heterocyclicthio group where the heterocyclic moiety is an optionally methyl substituted thiadiazolyl, tetrazolyl group or the heterocyclicthio group has the formula

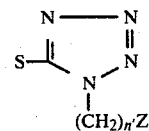

wherein Z is

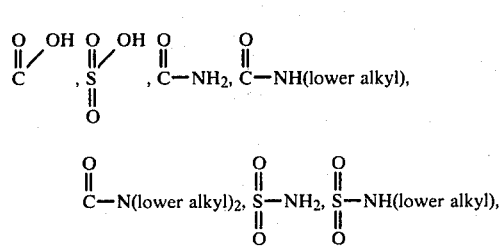

and n' is an integer of from one to four.

When n is two to four the acyl groups may be the same or different. When the acyl group is substituted by more than one group, the substituents may be the same or different.

Included within the above definition for N-acyl are cyclic structures incorporating the nitrogen atom by displacement of the hydrogen atom, such as the pyroglutamyl group, prolyl group, etc.

The carbon atoms may be part of a configuration which is classified as an aliphatic, olefinic or aromatic grouping or mixture of both, such as a phenethyl group.

The preferred compounds are those wherein M is

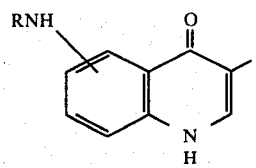

RNH is in the 6 or 7 position, R is $R_1$-[$NR_4$-acyl]$_n$, n is one and $R_3$ is 4-hydroxyphenyl.

Lower alkyl, where not specifically defined, is defined as a hydrocarbon fragment of from one to six carbon atoms. Lower alkoxy is equivalent to "lower alkyl-O-".

In accordance with the invention the foregoing amide compounds having the formula

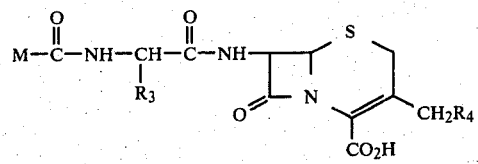

and pharmaceutically acceptable salts thereof wherein M, $R_3$ and $R_4$ are as previously defined are produced by reacting a compound of the formula

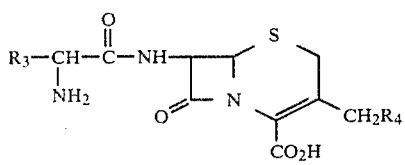

or the basic salt, silylated derivative (preferably the disilylated) thereof with a reactive derivative of a dihydro-oxo-3-quinoline carboxylic acid compound having the formula

M—CO$_2$H or its acid addition salts, wherein M, R$_4$ and R$_3$ are as previously defined.

Some examples of reactive derivatives of the substituted-dihydro-oxo-3-quinolinecarboxylic acid compound suitable for the reaction are the acid halides (especially the acid chloride), the imidazolide, mixed anhydrides (especially those from an alkyl chloroformate such as methyl, ethyl, and isobutyl chloroformate or pivaloyl chloride), and activated esters such as the pentachlorophenyl ester and N-hydroxysuccinimide ester.

The reactants are normally employed in approximate equimolar quantities, although an excess of either (oxoquinoline carboxylic acid compound or cephalosporin compound) can be used if desired. The reaction can be carried out in any of a number of unreactive solvents. When using a silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, when using the cephalosporin compounds in the free acid or salt form, aqueous solutions may be used for acylation with an acid halide or mixed anhydride under normal Schotten-Baumann conditions. The duration and temperature of the reaction are not critical. Temperatures in the range from −30° to +30° C. are commonly used for reaction times ranging from a few hours up to a day or more. The product may be isolated in any suitable way as the free acid or as a salt by appropriate adjustment of the pH.

The reactive derivative of substituted-dihydro-oxo-3-quinolinecarboxylic acid compounds and acid-addition salts which are required as starting materials in the foregoing process can be prepared according to any of a variety of methods.

A substituted-dihydro-oxo-3-quinolinecarboxylic acid may be converted to its acid chloride utilizing thionyl chloride, its mixed anhydride utilizing ethyl chloroformate, its pentachlorophenyl ester by esterication with pentachlorophenol and its imidazolide by reacting the acid with 1,1'-carbonyldiimidazole.

Compounds of the formula

M—CO$_2$H wherein M is as previously defined except wherein R$_1$ is hydrogen are prepared by acylation of a compounds of the formulae

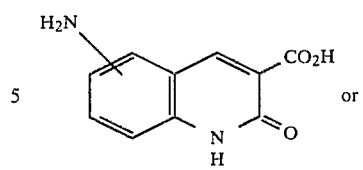

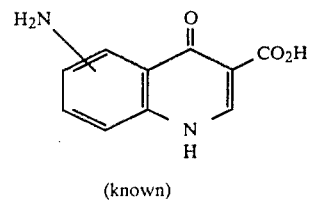

by a compound of the formula

R—OH wherein R is as previously defined except where R$_1$ is hydrogen.

The compound of the formula

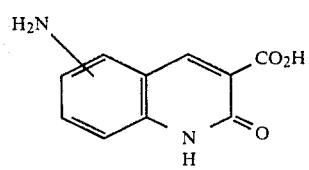

is prepared by hydrogenating of a compound of the formula

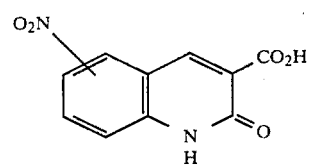

which is in turn prepared by nitration and deesterification of the known compound of the formula

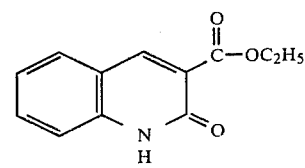

The silylated amino acid starting materials can be prepared by reacting an amino acid of the formula

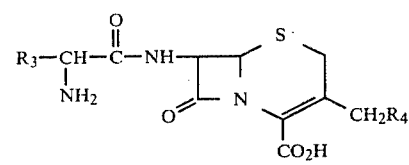

or a salt thereof wherein R$_3$ is as previously defined in anhydrous form with either one or two equivalents of a tri(lower alkyl)silyl chloride in the presence of triethylamine. The preferred silylating agents are trimethylsilyl chloride and dimethyl dichlorosilane. In all probability when two equivalents of the silylating agent are used, both the amino and the carboxyl group become silylated. When one equivalent is used, only the carboxyl group is silylated. Both the mono- and disilylated products are fully reactive with the activated acids. The disilylated product is preferred over the monosilylated product as a starting material. After acylation the silyl groups are easily removed by treatment with water.

Also in accordance with the invention, the compounds of this invention may be produced by reacting a free amino acid of the formula

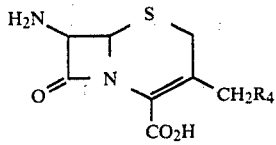

or the corresponding acid salt or silylated derivative thereof with a reactive derivative of D-N-[(substituted)-dihydro-oxo-quinolinylcarbonyl]-2-substituted glycine having the formula

or its acid addition salts where M and $R_3$ have the aforementioned significance.

Some examples of reactive derivatives of the D-N-(dihydro-oxo-3-quinolinylcarbonyl)-2-substituted glycine compounds suitable for the reaction are the acid halides, mixed anhydrides (especially those formed from an alkyl chloroformate such as ethyl chloroformate and isobutyl chloroformate), and activated esters such as the pentachlorophenyl ester and N-hydroxysuccinimide ester. Since racemization is more likely with the acid halide, the other forms are generally preferred. The reactants are normally employed in approximate equimolar quantities, although an excess of either (quinolinylcarboxylic acid compound or cephalosporanic acid compound) can be used if desired. The reaction can be carried out in any of a number of unreactive solvents. When using the silylated derivative for the reaction the solvent should be anhydrous and may include tertiary amides (such as N,N-dimethylacetamide, dimethylformamide, and N-methyl-2-pyrrolidinone), ethers (such as dioxane, tetrahydrofuran, and 1,2-dimethoxyethane), chlorinated hydrocarbons (such as chloroform and dichloromethane), and mixtures of these. In addition to any of these solvents, 7-aminocephalosporanic acid may be reacted with an acid chloride or mixed anhydride in the free acid or salt form using aqueous solutions under normal Schotten Baumann conditions. The duration and temperature of the reaction are not critical. Temperatures in the range from $-30°$ to $+30°$ C. are commonly used for reaction times ranging from a few house up to a day or more. The product may be isolated in any suitable way as the free acid or as a salt by appropriate adjustment of the pH.

The reactive derivative of D-N-[(substituted)-dihydro-oxo-3-quinolinylcarbonyl]-2-substituted glycines or their acid-addition salts which are required as starting materials in the foregoing process can be prepared by methods illustrated in greater detail hereinafter.

D-N-[(substituted)-dihydro-oxo-3-quinolinylcarbonyl]-2-substituted glycine compounds may be prepared by reacting the corresponding reactive derivative of said acid, such as the acid chloride, with the appropriate D-N-(trimethylsilyl)-2-substituted glycine, trimethylsilyl ester in the presence of triethylamine followed by hydrolysis.

The silylated amino acid starting materials can be prepared by reacting an anhydrous compound of the formula

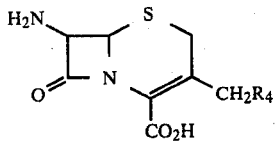

with a hexaalkyldisilazane. The preferred silylating agent is hexamethyldisilazane. Only the carboxyl group is silylated under the conditions used (e.g., 2-hour reflux in dichloromethane). After acylation, the silyl group is easily removed by treatment with water.

The free acids of the invention form carboxylate salts with any of a variety of inorganic and organic bases. Pharmaceutically acceptable carboxylate salts are formed by reacting the free acids with such bases as sodium hydroxide, sodium carbonate, sodium bicarbonate, sodium 2-ethylhexanoate, potassium hydroxide, potassium carbonate, potassium 2-ethylhexanoate, calcium hydroxide, ethylamine, 2-hydroxyethylamine, and procaine. Preferred carboxylate salt forms are the alkali metal salts. The carboxylate salts are converted to the free acids by acidification. The free acids and their carboxylate salts usually differ somewhat in solubility properties but, in general, are otherwise equivalent for the purposes of the invention. In addition, certain of the compounds of the invention can exist in the form of an acid-addition salt pharmaceutically acceptable salts are formed by reaction of the free base of a carboxylate salt with any of a number of inorganic and organic acids, including hydrochloric, sulfuric, nitric, phosphoric, acetic, benzoic, citric, maleic, malic, tartaric, succinic, gluconic, ascorbic, sulfamic, pamoic, methanesulfonic, benzenesulfonic and related acids.

When forming salts certain compounds may form mono, di, or tri, etc., salts. All of these compounds are intended to be equivalent for the purposes of the invention are intended to fall within the scope of the invention.

The compounds of the invention can exist in anhydrous form, as well as in solvated, including hydrated, forms. In general, the hydrated forms and the solvated forms with pharmaceutically acceptable solvents are equivalent to the anhydrous or unsolvated forms for the purposes of the invention.

The oxo-quinoline segment of the compounds of this invention may be capable of undergoing keto-enol tautomerism to give hydroxyquinolines. Such a tautomer is equivalent to the oxo-quinoline for the purposes of the inventions and are included within the above shown structures.

The compounds of the present invention can exist in various stereoisomeric forms. More specifically, the newly introduced amino acid fragments of the compounds may be in the form of the D-isomer, L-isomer or a mixture thereof [DL-mixture (partial or complete racemization)]. The invention is intended to include all of the isomeric forms and mixtures thereof. Even when a specific form is cited, small amounts of its stereoisomer may be present, since racemization may occur during the various steps in preparing the compound.

The compounds of the invention are new chemical compounds that are used as pharmacological agents and especially as broad spectrum antibacterial agents. They are active in vitro against strains of both gram-positive and gram-negative bacteria. The activity of the compounds is illustrated by the results shown in the table for certain of the preferred compounds.

Thus, the compounds of this invention and their non-toxic pharmaceutically acceptable salts are highly useful as broad spectrum antibiotics in mammals when administered in amounts ranging from about 5 mg to about 100 mg per kg of body weight per day. A preferred dosage regimen for optimum results would be from about 10 mg to about 50 mg per kg of body weight per day, and such dosage units are employed that a total of about 700 mg to about 3500 mg of active ingredient for a subject of about 70 kg body weight are administered in a 24 hour period in an appropriate pharmaceutical composition.

While the compounds of this invention may be administered orally in the form of tablets, capsules, syrups, etc., the preferred route of administration is parenterally for treating systemic infections.

In the present invention the term "pharmaceutical composition" is defined as a finished pharmaceutical that may in administered directly or a pharmaceutical which water is added to prior to use in order to form a satisfactory product for administration. The pharmaceutical compositions to be employed parenterally are generally supplied in a dry, sterile form having about 50 mg to about 1000 mg of active compound per vial. The vial may also contain other active ingredients, buffers, salts, etc. The sterile material in the vial is dissolved in water for injection at the time of use. Oral preparations would also have from about 50 mg to about 1000 mg of active compound per unit dose form.

The invention is illustrated by the following examples.

anhydride is added to the cold silylated quinoline and stirred with cooling for 3 hours and overnight at room temperature. the reaction mixture is treated with water. The solid is filtered to give 3.98 g of 7-[[L-2-(acetylamino)-1-oxopropyl]amino]-1,4-dihydro-4-oxo-3-quinolinecarboxylic acid.

$[\alpha]_D^{23} 0.8°$ (cl, DMSO).

A mixture of 2.22 g (7.0 mmol) of the above acid, 2.30 g (14.2 mmol) of carbonyldiimidazole, and 40 ml of dimethylformamide is heated at 53°–57° C. for 30 minutes and is stirred at room temperature overnight. The solution is diluted with 200 ml of ether. The solid is filtered to give 1.58 g of 7-[[L-2-(acetylamino)-1-oxopropyl]amino]-1,4-dihydro-4-oxo-3-quinolinecarboxylic acid imidazolide.

STARTING MATERIAL B

7-[[L-2-(Acetylamino)-5-amino-1,5-dioxopentyl]amino]-1,4-dihydro-4-oxo-3-quinolinecarboxylic acid imidazolide A mixture of 11.96 g (63.5 mmol) of N-acetyl-L-glutamine, 10.43 ml (42.6 mmol) of bis(trimethylsilyl)acetamide and 201 ml of tetrahydrofuran is stirred at 27° C. overnight and 2.44 ml (31.4 mmol) of N,N-dimethylformamide is added to the resulting solution. This solution is cooled to −34° C. and a cold solution of 2.26 ml (31.5 mmol) of thionyl chloride and 20 ml of dichloromethane is added and the reaction solution is stirred at −35° C. for 1.5 hours.

A mixture of 5.00 g (24.5 mmol) of 7-amino-1,4-dihydro-4-oxo-3-quinolinecarboxylic acid, 9.9 ml (73.5 mmol) of chlorotrimethylsilane, 10.28 ml (73.5 mmol) of triethylamine and 125 ml of dichloromethane is stirred at room temperature for 1 day and is filtered. The filtrate is added to the above acid chloride solution at −34° C. over 55 minutes and the reaction mixture is stirred at −34° C. for 2 hours. The reaction mixture is refrigerated at −30° C. overnight and then concentrated at 38° C. with a rotary evaporator. The residual semi-solid is treated with cold ethanol and filtered. The

ACTIVITY TABLE I

| A sodium salt of a compound of Example | Pseudomonas | | E. Coli | | Prot Vulg. | Entero Cloac. IM 11 | Serr. Mar. IMM 16 | Klebs. Pneum. MGH 2 | Strep. fec. MGH 2 | Staph | |
|---|---|---|---|---|---|---|---|---|---|---|---|
| | BRK #28 | UI 12-4-4 18 | Brig | Vogel | | | | | | UC76 | S 18713 |
| 1. | 3.1 | 6.3 | 3.1 | >50 | 0.8 | 0.8 | 6.3 | 3.2 | 0.8 | >50 | 6.3 | 12.5 |
| 2. | 3.1 | 3.1 | 6.3 | >50 | 0.4 | 3.1 | 3.1 | 0.3 | 0.4 | 25 | 3.1 | 6.3 |
| 3. | 3.1 | 6.3 | 3.1 | 12.5 | 1.6 | 6.3 | 12.5 | 50 | 1.6 | 25 | 3.1 | 6.3 |
| 4. | 3.1 | 6.3 | 12.5 | >50 | 0.8 | 6.3 | 12.5 | >50 | 3.1 | 25 | 3.1 | 6.3 |
| 5. | 3.1 | 6.3 | 6.3 | >50 | 0.4 | 3.1 | 3.1 | 6.3 | 0.8 | 25 | 3.1 | 6.3 |
| 6. | 6.3 | 12.5 | 12.5 | 6.3 | 0.8 | 6.3 | 6.3 | 25 | 1.6 | | 0.8 | 3.1 |
| 7. | 6.3 | 12.5 | 6.3 | 12.5 | 1.6 | 3.1 | 12.5 | 25 | 3.1 | | 1.6 | 6.3 |
| 8. | 3.1 | 6.3 | 3.1 | 50 | 6.3 | 25 | 25 | >50 | 25 | | 3.1 | 6.3 |

STARTING MATERIAL A

7-[[L-2-(Acetylamino)-1-oxopropyl]amino]-1,4-dihydro-4-oxo-3-quinolinecarboxylic acid imidazolide A mixture of 3.93 g (30 mmol) of N-acetyl-L-alanine, 3.30 ml (30 mmol) of N-methylmorpholine, 2.33 ml (30 mmol) of methyl chloroformate, and 80 ml of acetonitrile is stirred at −10° C. to −20° C. for 30 minutes. A mixture of 4.08 g (20 mmol) of 7-amino-1,4-dihydro-4-oxo-3-quinolinecarboxylic acid [J. Am. Chem. Soc., 69, 371 (1947)], 8.4 ml (60 mmol) of triethylamine, 7.6 ml (60 mmol) of chlorotrimethylsilane, and 100 ml of dichloromethane is stirred at room temperature for 30 minutes and then cooled to −20° C. The cold mixed solid is washed with water, ethanol and ether and dried to give 1.84 g of the title compound.

$[\alpha]_D^{23} + 18.0°$ (cl, DMSO).

| UV (MeOH) | 314 nm | $a_1^1$ 243 |
|---|---|---|
| | 270 | 589 |

A mixture of 1.0 g (2.67 mmol) of the above quinolinecarboxylic acid, 0.606 g (3.74 mmol) carbonyldiimidazole and 10 ml of N,N-dimethylacetamide is stirred at 60° C. for 50 minutes. The cooled solution is poured into a mixture of dichloromethane-ether and the precipitated solid is filtered and washed with the dichloromethane-ether mixture to give 0.88 g of 7-[[L-2-(acetylamino)-5-amino-1,5-dioxopentyl]amino]-1,4-dihydro-4-oxo-3-quinolinecarboxylic acid imidazolide.

$[\alpha]_D^{23} + 15.2°$ (cl, DMSO).

STARTING MATERIAL C 1,4-Dihydro-4-oxo-7-[[(L-5-oxo-2-pyrrolidinyl)carbonyl]amino]-3-quinolinecarboxylic acid imidazolide A mixture of 3.87 g (30 mmol) of 5-oxo-L-proline, 2.32 ml (30 mmol) of dimethylformamide, 2.19 ml (30 mmol) of thionyl chloride, and 75 ml of dichloromethane is stirred with cooling for 50 minutes. A mixture of 4.08 g (20 mmol) of 7-amino-1,4-dihydro-4-oxo-3-quinolinecarboxylic acid, 8.4 ml (60 mmol) of triethylamine, 7.6 ml (60 mmol) of chlorotrimethylsilane, and 200 ml of dichloromethane is stirred at room temperature for 50 minutes and then cooled to 0° C. The cold acid chloride solution is added to the cold silylated quinoline and is stirred with cooling for 3 hours and at room temperature overnight. The reaction mixture is evaporated to dryness and the residue is treated with water and ethanol. The solid is filtered to give 4.72 g of 1,4-dihydro-4-oxo-7-[[(5-oxo-2-pyrrolidinyl)carbonyl]amino]-3-quinolinecarboxylic acid.

$[\alpha]_D^{23} + 13°$ (cl, DMSO).

A mixture of 4.70 g (14.9 mmol) of the above quinoline acid, 4.83 g (29.8 mmol) of carbonyldiimidazole, and 40 ml of dimethylformamide is stirred at 51°–54° C. for 35 minutes and at room temperature overnight. The solution is evaporated and the residue is treated with acetonitrile. The solid is filtered to give 4.60 g of 1,4-dihydro-4-oxo-7-[[(L-5-oxo-2-pyrrolidinyl)carbonyl]amino]-3-quinolinecarboxylic acid imidazolide.

$[\alpha]_D^{23} + 5.5°$ (cl, DMSO).

STARTING MATERIAL D

6-[[L-2-(Acetylamino)-1-oxopropyl]amino]-1,4-dihydro-4-oxo-3-quinolinecarboxyl acid imidazolide A mixture of 1.73 g (13.2 mmol) of N-acetyl-L-alanine, 0.97 ml (13.2 mmol) of thionyl chloride, 1.02 ml (13.2 mmol) dimethylformamide, and 50 ml of dichloromethane is stirred at −20° C. to −30° C. for 20 minutes. A mixture of 2.45 g (12 mmol) of 6-amino-1,4-dihydro-4-oxo-3-quinolinecarboxylic acid [J. Pharm. Sci., 11, 1051 (1963)], 5.04 ml (36 mmol) triethylamine, 4.57 ml (36 mmol) chlorotrimethylsilane and 100 ml of dichloromethane is stirred at room temperature for 25 minutes and is cooled to −60° C. The cold acid chloride solution is added to the cold silylated quinoline and is stirred for 2 hours while the temperature comes up to 10° C. The reaction mixture is evaporated to dryness and the residue is treated with water to give 2.60 g of 6-[[L-2-(acetylamino)-1-oxopropyl]amino]-1,4-dihydro-4-oxo-3-quinolinecarboxylic acid, mp 196°–200° C.

$[\alpha]_D^{23} + 40.5°$ (cl, DMSO).

| UV (pH 7) | 309 nm | $a_1^1$ | 301 |
|---|---|---|---|
| | 255 | | 1050 |

A mixture of 2.20 g (6.93 mmol) of the above quinoline acid, 2.25 g (13.9 mmol) of carbonyldiimidazole and 20 ml of dimethylformamide is stirred at 51° C. to 53° C. for 35 minutes and at room temperature overnight. The solution is diluted with 80 ml of acetonitrile and 80 ml of ether. The solid is filtered to give 2.42 g of 6-[[L-2-(acetylamino)-1-oxopropyl]amino]-1,4-dihydro-4-oxo-3-quinolinecarboxylic acid imidazolide.

STARTING MATERIAL E 1,2-Dihydro-6-nitro-2-oxo-3-quinolinecarboxylic acid

A solution of 10.0 g (46 mmol) of 1,2-dihydro-2-oxo-3-quinolinecarboxylic acid, ethyl ester [J. Chem. Soc., 2518 (1962)] and 50 ml of sulfuric acid is stirred in an ice bath and a cold mixture of 9.75 ml of 70% nitric acid and 9.75 ml of sulfuric acid is added dropwise over 10 minutes. The reaction solution is stirred with ice bath cooling for 1 hour and then is poured into ice and water with stirring. The resulting solid is collected by filtration and washed with water and ethanol. After drying, 10.7 g of the requisite ester is obtained, mp>310° C. The structure is assigned by an unequivocal synthesis from the condensation of 2-amino-5-nitro-benzaldehyde and diethyl malonate to give the same 1,2-dihydro-6-nitro-2-oxo-3-quinolinecarboxylic acid, ethyl ester.

A mixture of 9.7 g (37 mmol) of the above ester and 200 ml of 1 N sodium hydroxide is heated on the steam bath for 1¼ hours. The resulting suspension is poured over ice and acidified with 250 ml of 1 N hydrochloric acid. The solid is collected by filtration and washed with water and ethanol to give 8.15 g of the title acid, mp>310° C.

6-Amino-1,2-dihydro-2-oxo-3-quinolinecarboxylic acid

A solution of 3.63 g (14.9 mmol) of 1,2-dihydro-6-nitro-2-oxo-3-quinolinecarboxylic acid and 200 ml of dimethylformamide is hydrogenated using 1 g of Raney nickel catalyst at 52 psi and 23° until the required amount of hydrogen uptake is obtained. The catalyst is filtered off and the filtrate is evaporated to dryness. The residue is treated with ethanol and 3.0 g of the desired product and is filtered.

| UV (pH 7) | 367 nm | $a_1^1$ | 257 |
|---|---|---|---|
| | 243 | | 1410 |

6-[[L-2-(Acetylamino)-1-oxopropyl]amino]-1,2-dihydro-2-oxo-3-quinolinecarboxylic acid imidazolide A mixture of 3.06 g (15 mmol) of 6-amino-1,2-dihydro-2-oxo-3-quinolinecarboxylic acid, 120 ml of dichloromethane, 6.3 ml (45 mmol) chlorotrimethylsilane, and 5.7 ml (45 mmol) of triethylamine is stirred for 30 minutes at room temperature, then cooled to −50° C. A mixture of 2.95 g (22.5 mmol) of N-acetyl-L-alanine, 80 ml of dichloromethane, 1.74 ml (22.5 mmol) of dimethylformamide, and 1.65 ml (22.5 mmol) of thionyl chloride is stirred at −30° C. to −40° C. for 25 minutes. The resulting solution is added to the cold silylated quinoline and is stirred with cooling for 2 hours and at room temperature overnight. The reaction mixture is evaporated, and the residue is treated with methanol. The solid is collected to yield 1.42 g of 6-[[(L-2-(acetylamino)-1-oxopropyl]-amino]-1,2-dihydro-2-oxo-3-quinolinecarboxylic acid.

A mixture of 1.35 g (4.25 mmol) of the above quinoline acid, 1.38 g (8.9 mmol) of carbonyldiimidazole and 15 ml of dimethylformamide is heated at 45°–48° C. for ½ hour and is stirred overnight at room temperature. The solution is evaporated to a gum which is treated with acetonitrile. The solid is collected to yield 1.25 g of 6-[[L-2-(acetylamino)-1-oxopropyl]amino]-1,2-dihydro-2-oxo-3-quinoline carboxylic acid imidazolide.

STARTING MATERIAL F

8-Amino-1,4-dihydro-4-oxo-3-quinolinecarboxylic acid

A solution of 15.0 g (64 mmol) of 1,4-dihydro-8-nitro-4-oxo-3-quinolinecarboxylic acid [J. Amer. Chem. Soc. 68, 1264 (1946)] in 300 ml of dimethylformamide is hydrogenated using 1 g of Raney nickel catalyst at 51 psi and 23° C. until the required amount of hydrogen uptake is obtained. The catalyst is filtered off and the filtrate is concentrated to 50 ml and ethanol is added. The solid is collected by filtration and washed with ethanol and ether to give 9.7 g of the title compound.

| UV (pH 7) | 327 nm | $a_1^1$ 362 |
|---|---|---|
|  | 238 | 1370 |

EXAMPLE 1

N-[7-[[L-2-(Acetylamino)-1-oxopropyl]amino]-1,4-dihydro-4-oxo-3-quinolinylcarbonyl]-7-[D-2-amino-2-phenylacetamido]-3-[[(1-sulfomethyl-1H-tetrazol-5-yl)thio]methyl]-3-cephem-4-carboxylic acid A mixture of 3.39 g (5 mmol) of 7-[D-2-amino-2-phenylacetamido]-3-[[(1-sulfomethyl-1H-tetrazol-5-yl)thio]methyl]-3-cephem-4-carboxylic acid, sodium salt (U.S. Pat. No. 4,048,311), 2.04 g (5 mmol) of 7-[[L-2-(acetylamino)-1-oxopropyl]amino]-1,4-dihydro-4-oxo-3-quinoline carboxylic acid imidazolide, 1.6 ml (5.12 mmol) of 3.2 M sodium 2-ethylhexanoate in N,N-dimethylacetamide and 15 ml of N,N-dimethylacetamide is stirred at 0° C. for ½ hour and at room temperature for 1½ hours. The solution is added to 200 ml of ethyl acetate with stirring. The solid is filtered and washed with ethyl acetate and ether. The dried solid is dissolved in 100 ml of cold water and the solution is titrated to pH 7 with 2 N hydrochloric acid. The solution is filtered and lyophilized to give 4.78 g of the disodium salt of the title compound.

$[\alpha]_D^{23} + 4.5°$ (cl, pH 7).

| UV (pH 7) | 275 nm | $a_1^1$ 666 |
|---|---|---|
|  | 240 | 264 |
|  | 268 | 604 |
|  | 311 | 123 |
|  | 324 | 75 |

EXAMPLE 2

N-[7-[[L-2-(Acetylamino)-1-oxopropyl]amino]-1,4-dihydro-4-oxo-3-quinolinylcarbonyl]-7-[D-2-amino-2-(4-hydroxyphenyl)acetamido]-3-[[(1-methyl-1H-tetrazol-5-yl)thio]methyl]-3-cephem-4-carboxylic acid A mixture of 2.2 g (6 mmol) of 7-[[L-2-(acetylamino)-1-oxopropyl]amino]-1,4-dihydro-4-oxo-3-quinolinecarboxylic acid imidazolide, 3.3 g (6 mmol) of 7-[D-2-amino-2-(4-hydroxyphenyl)acetamido]-3-[[(1-methyl-1H-tetrazol-5-yl)thio]methyl]-3-cephem-4-carboxylic acid [J. Antibiot., 29, 65 (1976)], and 25 ml of N,N-dimethylacetamide is stirred at room temperature for 3 hrs and 4 ml (13 mmole) of 3.3 M sodium 2-ethyl-hexanoate in N,N-dimethylacetamide is added. The solution is poured into 300 ml of ethyl acetate with stirring and the solid is collected and washed with ethyl acetate and ether to give 3.3 g of the sodium salt of the title compound.

$[\alpha]_D^{23} + 11.6°$ (cl, pH 7).

| UV (pH 7) | 274 nm | $a_1^1$ 621 |
|---|---|---|
|  | 236 | 288 |

EXAMPLE 3

N-[7-[[L-2-(Acetylamino)-1-oxopropyl]amino]-1,4-dihydro-4-oxo-3-quinolinylcarbonyl]-7-[D-2-amino-2-(4-hydroxyphenyl)acetamido]-3-acetoxymethyl-3-cephem-4-carboxylic acid A mixture of 2.04 g (5.0 mmol) of 7-[[L-2-(acetylamino)-1-oxopropyl]amino]-1,4-dihydro-4-oxo-3-quinolinecarboxylic acid imidazolide, 2.40 g (5.25 mmol) of 7-[D-2-amino-2-(4-hydroxyphenyl)acetamido]-3-acetoxymethyl-3-cephem-4-carboxylic acid [J. Antibiot., 29, 65 (1976)], 0.70 ml (5.0 mmol) of triethylamine and 30 ml of N,N-dimethylacetamide is stirred at room temperature for 5 hours and 0.9 ml (6.5 mmol) of triethylamine is added. The solution is poured into 300 ml of vigorously stirred ethyl acetate. The solid is filtered off and washed with ethyl acetate and ether. The solid is dissolved with 100 ml of water and acidified to pH 2 with 1 N hydrochloric acid. The solid is filtered off and suspended in 500 ml of water and 1 N sodium hydroxide is added to pH 6.5. The solution is filtered and lyophilized to give 3.40 g of the sodium salt of the title compound.

$[\alpha]_D^{23} + 32.1°$ (cl, pH 7).

| UV (pH 7) | 275 nm | $a_1^1$ 829 |
|---|---|---|
|  | 239 | 356 |

EXAMPLE 4

N-[7-[[L-2-(Acetylamino)-5-amino-1,5-dioxopentyl]amino]-1,4-dihydro-4-oxo-3-quinolinylcarbonyl]-7-[D-2-amino-2-(4-hydroxyphenyl)acetamido]-3-acetoxymethyl-3-cephem-4-carboxylic acid A mixture of 1.26 g (2.75 mmol) of 7-[D-2-amino-2-(4-hydroxyphenyl)acetamido]-3-acetoxymethyl-3-cephem-4-carboxylic acid [J. Antibiot., 29, 65 (1976)], 1.11 g (2.62 mmol) of 7-[[L-2-(acetylamino)-5-amino-1,5-dioxopentyl]amino]-1,4-dihydro-4-oxo-3-quinolinecarboxylic acid imidazolide, 0.37 ml (2.62 mmol) of triethylamine, and 20 ml of N,N-dimethylacetamide is stirred at 0° C. for 2 hours and at room temperature for 3 hours. The solution is poured into 200 ml of ice water and acidified to pH 2 with dilute hydrochloric acid. The solid is filtered and washed with water. The solid is suspended in water and 1 N sodium hydroxide is added to pH 6.9. The solution is filtered and lyophilized to give 0.57 g of the sodium salt of the title compound.

$[\alpha]_D^{23} + 4°$ (cl, DMSO).

| UV (pH 7) | 274 nm | $a_1^1$ 733 |
|---|---|---|
|  | 237 | 331 |

EXAMPLE 5

N-[7-[[L-2-(Acetylamino)-5-amino-1,5-dioxopentyl]amino]-1,4-dihydro-4-oxo-3-quinolinylcarbonyl]-7-[D-2-amino-2-(4-hydroxyphenyl)acetamido]-3-[[(1-methyl-1H-tetrazol-5-yl)thio]methyl]-3-cephem-4-carboxylic acid A mixture of 2.32 g (4.4 mmol) of 7-[D-2-amino-2-(4-hydroxyphenyl)acetamido]-3-[[(1-methyl-1H-tetrazol-5-yl)thio]methyl]-3-cephem-4-carboxylic acid [J. Antibiot., 29, 65 (1976)], 1.79 g (4.2 mmol) of 7-[[L-2-(acetylamino)-5-amino-1,5-dioxopentyl]amino]-1,4-dihydro-4-oxo-3-quinolinecarboxylic acid imidazolide, 1.18 ml (8.4 mmol) of triethylamine, and 20 ml of N,N-dimethylacetamide is stirred at 0° C. for 2 hours and room temperature for 2 hours. stirred at 0° C. for 2 hours and room temperature for 2 hours. The solution is poured into 200 ml of cold water and acidified to pH 2 with dilute hydrochloric acid. The solid is filtered and washed with water. The solid is suspended in 100 ml of water and 1 N sodium hydroxide is added to pH 6.5. The solution is filtered and lyophilized to give 2.21 g of the sodium salt of the title compound.

$[\alpha]_D^{23} - 33.4°$ (cl, pH 7).

| UV (pH 7) | 274 nm | $a_1^1$ 653 |
|---|---|---|
| | 234 | 311 |

EXAMPLE 6

N-[1,4-Dihydro-4-oxo-7-[[(L-5-oxo-2-pyrrolidinyl)carbonyl]amino]-3-quinolinylcarbonyl]-7-[D-2-amino-2-phenylacetamido]-3-[[(1-methyl-1H-tetrazol-5-yl)thio]methyl]-3-cephem-4-carboxylic acid A mixture of 1.83 g (5 mmol) of 1,4-dihydro-4-oxo-7-[[(L-5-oxo-2-pyrrolidinyl)carbonyl]amino]-3-quinolinecarboxylic acid imidazolide; 4.21 g (5.5 mmol) of 7-[D-2-amino-2-phenylacetamido]-3-[[(1-methyl-1H-tetrazol-5-yl)thio]methyl]-3-cephem-4-carboxylic acid 1.5 p-toluenesulfonic acid salt [J. Antibiot., 29, 65 (1976)], 1.16 ml (8.25 mmol) of triethylamine and 25 ml of N,N-dimethylacetamide is stirred at room temperature for 3½ hours and 0.91 ml (6.5 mmol of triethylamine is added to the solution. The solution is poured into 300 ml of ethyl acetate. The solid is filtered and washed with ethyl acetate and ether. The solid is dissolved in 250 ml of water and 1 N hydrochloric acid is added to pH 1.5. The solid is filtered and suspended in 150 ml of water and 1 N sodium hydroxide is added to pH 7.5. The solution is filtered and lyophilized to give 1.8 g of crude product. The solid is dissolved with 9 ml of cold water and with ice bath cooling, 75 ml of acetone is added. The dark solid is filtered and 100 ml of acetone is added to the filtrate. This solid is filtered and washed with ether. The solid is dissolved in 100 ml of water and lyophilized to give 0.83 g of the sodium salt of the title compound.

$[\alpha]_D^{23} - 27°$ (cl, pH 7).

| UV (pH 7) | 272 nm | $a^1$ 633 |
|---|---|---|

EXAMPLE 7

N-[6-[[L-2-(Acetylamino)-1-oxopropyl]amino]-1,4-dihydro-4-oxo-3-quinolinylcarbonyl]-7-[D-2-amino-2-phenylacetamido]-3-[[(1-methyl-1H-tetrazol-5-yl)thio]methyl]-3-cephem-4-carboxylic acid A mixture of 1.84 g (5.0 mmol) of 6-[[L-2-(acetylamino)-1-oxopropyl]amino]-1,4-dihydro-4-oxo-3-quinolinecarboxylic acid imidazolide, 4.21 g (5.5 mmol) of 7-[D-2-amino-2-phenylacetamido]-3-[[(1-methyl-1H-tetrazol-5-yl)thio]methyl]-3-cephem-4-carboxylic acid 1.5 p-toluenesulfonic acid salt [J. Antibiot., 20, 65 (1976)], 1.16 ml (8.25 mmol) of triethylamine, and 25 ml of N,N-dimethylacetamide is stirred at 0° for 1.75 hrs and at room temperature for 1.3 hrs and 0.91 ml (6.5 mmol) of triethylamine is added. The solution is poured into 300 ml of ethyl acetate and the solid is filtered and washed with ethyl acetate and ether. The solid is dissolved in 300 ml of water, filtered, and acidified to pH 2 with 1 N hydrochloric acid. The solid is suspended in 150 ml of water and 1 N sodium hydroxide is added to pH 6.9 and the solution is filtered and lyophilized to give 3.4 g of the sodium salt of the title compound.

$[\alpha]_D^{23} - 47.5°$ (cl, pH 7).

| UV (pH 7) | 312 nm | $a_1^1$ 173 |
|---|---|---|
| | 264 | 488 |
| | 258 | 488 |
| | 230 | 496 |

EXAMPLE 8

N-[6-[[L-2-(Acetylamino)-1-oxopropyl]amino]-1,2-dihydro-2-oxo-3-quinolinylcarbonyl]-7-[D-2-amino-2-(4-hydroxyphenyl)acetamido]-3-acetoxymethyl-3-cephem-4-carboxylic acid A mixture of 1.47 g (4.0 mmol) of 6-[[L-2-(acetylamino)-1-oxopropyl]amino]-1,2-dihydro-2-oxo-3-quinolinecarboxylic acid imidazolide, 1.83 g (4.0 mmol) of 7-[D-2-amino-2-(4-hydroxyphenyl)acetamido]-3-acetoxymethyl-3-cephem-4-carboxylic acid [J. Antibiot., 29, 65 (1976)], 0.56 ml (4.0 mmol) of triethylamine, and 25 ml of N,N-dimethylacetamide is stirred at room temperature for 4.5 hours. The solution is poured into 250 ml of ethyl acetate and the solid is filtered and washed with ethyl acetate and ether. The solid is dissolved in 100 ml water and acidified to pH 2 with 1 N hydrochloric acid. The solid is filtered and suspended in 150 ml of water and 1 N sodium hydroxide is added to pH 7 and the solution is filtered and lyophilized to give 2.6 g of the sodium salt of the title compound.

$[\alpha]_D^{23} - 42.8°$ (cl, pH 7).

| UV (pH 7) | 366 nm | $a_1^1$ 77 |
|---|---|---|
| | 253 | 559 |

We claim:
1. A compound of the formula

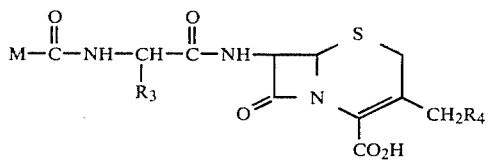

and pharmaceutically acceptable salts thereof; wherein M is

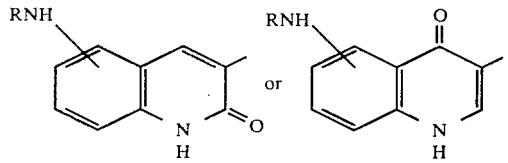

RNH is in the 6 or 7 position; R is

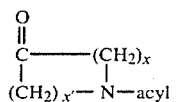

or $R_1$-$(R_5N$-acyl$)_n$; x is an integer from one to five, x' is zero, one or two; $R_1$ is hydrogen, lower alkyl, benzyl, or

wherein $R_2$ is hydrogen; amino or a lower alkyl group of from one to four carbon atoms, optionally substituted by from one to three chlorine or fluorine atoms; $R_5$ is hydrogen or lower alkyl and N-acyl is an aminoacyl moiety derived from a carboxylic acid of from two to ten carbon atoms optionally substituted by from one to three of the following groups, hydroxyl, carboxy,

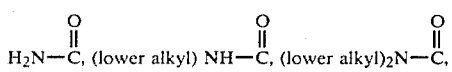

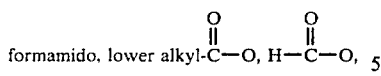

amino, alkylamido, carbamido, carbonyl oxygen, lower alkoxy, lower alkylthio or sulfonic acid, n is an integer of from one to four; $R_3$ is phenyl, 4-hydroxyphenyl, 2-thienyl or cyclohexa-1,4-dien-1-yl and $R_4$ is acetoxy, carbamoyloxy, or a heterocyclicthio group where the heterocyclic moiety is an optionally methyl substituted thiadiazolyl, tetrazolyl group or the heterocyclicthio group has the formula

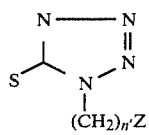

wherein Z is

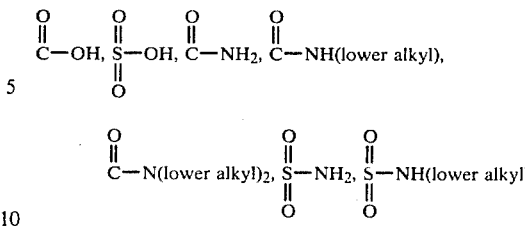

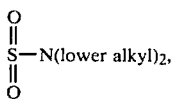

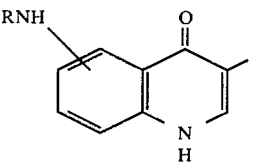

or $CH_2$-OH and n' is an integer of from one to four.

2. The compounds of claim 1 wherein M is

3. A compound of claim 2 wherein R is $R_1[NR_5$-acyl$]_n$.

4. A compound of claim 3 wherein n is one.

5. A compound of claim 4 wherein $R_3$ is 4-hydroxy phenyl.

6. A compound of claim 1 having the name N-[7-[[L--2-(acetylamino)-1-oxopropyl]amino]-1,4-dihydro-4-oxo-3-quinolinylcarbonyl]-7-[D-2-amino-2-phenylacetamido]-3-[[(1-sulfomethyl-1H-tetrazol-5-yl)-thio]-methyl]-3-cephem-4-carboxylic acid and pharmaceutically acceptable salts thereof.

7. A compound of claim 1 having the name N-[7 -[[L-2-(acetylamino)-1-oxopropyl]amino]-1,4-dihydro-4-oxo-3-quinolinylcarbonyl]-7-[D-2-amino-2-(4-hydroxyphenyl)acetamido]-3-[[(1-methyl-1H-tetrazol-5-yl)thio]methyl]-3-cephem-4-carboxylic acid and pharmaceutically acceptable salts thereof.

8. A compound of claim 1 having the name N-[7-[[L-2-(acetylamino)-1-oxopropyl]amino]-1,4-dihydro-4-oxo-3-quinolinylcarbonyl]-7-[D-2-amino-2-(4-hydroxyphenyl)acetamido]-3-acetoxymethyl-3-cephem-4-carboxylic acid and pharmaceutically acceptable salts thereof.

9. A compound of claim 1 having the name N-[ 7-[[L-2-(acetylamino)-5-amino-1,5-dioxopentyl]amino]-1,4-dihydro-4-oxo-3-quinolinylcarbonyl]-7-[D-2-amino-2-(4-hydroxyphenyl)acetamido]-3-acetoxymethyl-3-cephem-4-carboxylic acid and pharmaceutically acceptable salts thereof.

10. A compound of claim 1 having the name N-[7-[[L--2-(acetylamino)-5-amino-1,5-dioxopentyl]amino]-1,4--dihydro-4-oxo-3-quinolinylcarbonyl]-7-[D-2-amino-2-(4-hydroxyphenyl)acetamido]-3-[[(1-methyl-1H-tetrazol-5-yl)thio]methyl]-3-cephem-4-carboxylic acid and pharmaceutically acceptable salts thereof.

11. A compound of claim 1 having the name N-[1,4-dihydro-4-oxo-7-[[(L-5-oxo-2-pyrrolidinyl)carbonyl]-amino]-3-quinolinylcarbonyl]-7-[D-2-amino-2-phenylacetamido]-3-[[(1-methyl-1H-tetrazol-5-yl)thio]methyl]-3-cephem-4-carboxylic acid and pharmaceutically acceptable salts thereof.

12. A compound of claim 1 having the name N-[6-[[L-2-(acetylamino)-1-oxopropyl]amino]-1,4-dihydro-4-oxo-3-quinolinylcarbonyl]-7-[D-2-amino-2-phenylacetamido]-3-[[(1-methyl-1H-tetrazol-5-yl)thio]methyl]-3-cephem-4-carboxylic acid and pharmaceutically acceptable salts thereof.

13. A compound of claim 1 having the name N-[6-[[L-2-(acetylamino)-1-oxopropyl]amino]-1,2-dihydro-2-oxo-3-quinolinylcarbonyl]-7-[D-2-amino-2-(4-hydroxyphenyl)-acetamido]-3-acetoxymethyl-3-cephem-4-carboxylic acid and pharmaceutically acceptable salts thereof.

14. A pharmaceutical composition comprising an antibacterially-effective amount of a compound of claim 1 and a pharmaceutical carrier.

15. A method for treating infections which comprises administering the pharmaceutical composition of claim 14.

* * * * *